United States Patent [19]
Takuma et al.

[11] Patent Number: 4,594,449
[45] Date of Patent: Jun. 10, 1986

[54] PROCESS FOR PRODUCING TEREPHTHALIC ACID SUITABLE FOR USE IN DIRECT POLYMERIZATION

[75] Inventors: Toshiaki Takuma; Takayuki Tsumura; Takanori Tsugiya; Katsuya Murakami; Yasue Nakajima, all of Yokkaichi, Japan

[73] Assignee: Kuraray Yuka Co., Ltd., Tokyo, Japan

[21] Appl. No.: 556,161

[22] Filed: Nov. 29, 1983

[30] Foreign Application Priority Data

Dec. 3, 1982 [JP] Japan ................................ 57-212881

[51] Int. Cl.$^4$ ............................................ C07C 51/265
[52] U.S. Cl. ....................................... 562/416; 562/413
[58] Field of Search ................ 562/413, 416, 485, 487

[56] References Cited

U.S. PATENT DOCUMENTS

| | | | |
|---|---|---|---|
| 3,387,027 | 6/1968 | Alagy | 562/413 |
| 3,859,344 | 1/1975 | Shigeyasu et al. | 562/414 |
| 4,212,995 | 7/1980 | Shiraki | 562/485 |
| 4,286,101 | 8/1981 | Hashizume et al. | 562/487 |

FOREIGN PATENT DOCUMENTS

| | | |
|---|---|---|
| 2049227 | 4/1972 | Fed. Rep. of Germany ...... 562/416 |
| 0108946 | 9/1977 | Japan . |
| 0108947 | 9/1977 | Japan . |
| 2032920 | 5/1980 | United Kingdom . |
| 1598868 | 9/1981 | United Kingdom . |

*Primary Examiner*—Natalie Trousof
*Assistant Examiner*—Patricia M. Scott
*Attorney, Agent, or Firm*—Wenderoth, Lind & Ponack

[57] ABSTRACT

A process for producing terephthalic acid suitable for use in direct polymerization, which comprises oxidizing p-xylene with molecular oxygen in an acetic acid solvent in the presence of a heavy metal compound and a bromine compound, wherein after a main reaction step of oxidizing at least 90 mole % of p-xylene fed has been performed, (1) a first purifying step of feeding a gas containing molecular oxygen to the oxidation reaction mixture obtained from the main reaction step in such a proportion that the concentration of oxygen in the off-gas becomes at least 0.5% by volume and smashing the oxidation reaction mixture at a temperature of 140° to 230° C. to decrease the average particle diameter of terephthalic acid by at least 20% from its average particle diameter before smashing, and (2) a second purifying step of feeding a gas containing molecular oxygen to the slurry from the first purifying step in such a proportion that the concentration of oxygen in the off-gas becomes 0.05 to 5% by volume, and contacting the slurry with the molecular oxygen-containing gas at a temperature at least 10° C. higher than in the first purifying step and within the range of 180° to 300° C., are performed successively, and the resulting purified slurry is subjected to solid-liquid separation to recover terephthalic acid.

11 Claims, No Drawings

PROCESS FOR PRODUCING TEREPHTHALIC ACID SUITABLE FOR USE IN DIRECT POLYMERIZATION

This invention relates to a process for producing terephthalic acid of high purity, and more specifically, to a process for producing terephthalic acid suitable for use in preparing a polyester of high quality by direct polycondensation with a glycol.

A typical industrial process now in use for production of terephthalic acid comprises oxidizing p-xylene with a gas containing molecular oxygen in the presence of a heavy metal catalyst and a bromine compound (see, for example, U.S. Pat. No. 2,833,816). Terephthalic acid crystals obtained by this process usually contain impurities such as aldehydes and coloring materials, and cannot be used as such for direct polymerization with a glycol. Moreover, it is generally extremely difficult to separate the impurities from the terephthalic acid crystals.

Many methods have been proposed for the purification of terephthalic acid. They include, for example, (a) a method of purification by sublimation (see, for example, Japanese Patent Publications Nos. 7721/1961 and 5237/1961); (b) a method which comprises converting terephthalic acid to its salt or ester, purifying the salt or ester by a usual procedure such as recrystallization or distillation, and converting it back to terephthalic acid (see, for example, Japanese Patent Publication No. 53332/1982); (c) a method of purification by extraction with a suitable solvent such as water or acetic acid (see, for example, Japanese Patent Publications Nos. 3832/1973 and 26750/1973); and (d) a method which comprises contacting terephthalic acid in the form of a suspension in a solvent such as water, acetic acid or propionic acid with a gas containing molecular oxygen (see, for example, Japanese Patent Publications Nos. 12695/1965 and 21819/1967).

These methods, however, have one or more disadvantages. According to the method (a), the use of high temperatures causes decomposition of terephthalic acid or reduces its quality otherwise, and it is also disadvantageous in respect of the equipment that has to be used. The method (b) can give terephthalic acid of superior quality, but is not necessarily advantageous for industrial practice because an alcohol or an alkali must be used and the process steps are considerably complex. The method (c) cannot be said to be industrially advantageous because the extraction cannot give a product of high quality, and the recrystallization procedure requires a large amount of a solvent or high temperatures in order to dissolve terephthalic acid completely. The method (d) can give terephthalic acid of fairly superior quality, but the resulting terephthalic acid has a small particle size and a low apparent density and its particle shape is unsuitable for use in direct esterification with ethylene glycol. This is also true with the method (c). Furthermore, in all of these methods, terephthalic acid should be subjected to the purifying step after it has been separated from the reaction mixture. This entails a disadvantage in regard to the equipment used, and in this regard, too, these methods cannot be said to be advantageous for industrial practice.

In an attempt to overcome the defects and disadvantages of conventional methods such as those cited above, some methods have recently been proposed for producing terephthalic acid of high purity which can be used directly as a raw material for polyesters, for example terephthalic acid containing less than 500 ppm of 4-carboxybenzaldehyde, one typical impurity, economically advantageously in one plant by the oxidation reaction of p-xylene. For example, reoxidation of the oxidation reaction mixture at low temperatures has been proposed (see, for example Japanese Laid-Open Patent Publication No. 85136/1977 corresponding to Canadian Pat. No. 1,062,279, British Pat. No. 1,555,246, German Pat. No. 2,647,698 and French Pat. No. 2,328,688, and Japanese Laid-Open Patent Publication No. 37636/1978 corresponding to Canadian Pat. No. 1,079,297, British Pat. No. 1,589,310, German Pat. No. 2,741,382 and Belgian Pat. No. 858,814). This method has the disadvantage that the amount of the acetic acid solvent burnt during the oxidation reaction is large. Additional oxidation treatment of the oxidation reaction mixture at high temperatures has also been proposed (Japanese Laid-Open Patent Publication No. 55138/1980 corresponding to U.S. Pat. No. 4,286,101, British Pat. No. 2,032,920 and German Pat. No. 2,942,375, and Japanese Laid-Open Patent Publication No. 18647/1982). According to this method, terephthalic acid of high purity can be obtained with the burning of a relatively small amount of acetic acid. But since the temperature is extremely high, an enormous amount of thermal energy is required. Furthermore, burning of acetic acid, although reduced, cannot still be ignored.

Some of the present inventors made investigations about a process for economically producing terephthalic acid of high purity which can be directly reacted with a glycol component to form fiber-grade polyesters of high quality, and the achievements they made are disclosed in Japanese Patent Publications Nos. 5380/1981 and 6411/1981. Further investigations have now led to the discovery that by employing specified process conditions, terephthalic acid of high purity which contains only small amounts of aldehydes and coloring materials, has a low viscosity when slurried together with a glycol, and is suitable for direct polymerization can be obtained in spite of the fact that the amount of the acetic acid solvent burnt and the amount of thermal energy in a purification step following the oxidation step are small.

According to this invention, there is provided a process for producing terephthalic acid suitable for use in direct polymerization, which comprises oxidizing p-xylene with molecular oxygen in an acetic acid solvent in the presence of a heavy metal compound and a bromine compound, wherein after a main reaction step of oxidizing at least 90 mole % of p-xylene fed has been performed, (1) a first purifying step of feeding a gas containing molecular oxygen to the oxidation reaction mixture obtained from the main reaction step in such a proportion that the concentration of oxygen in the off-gas becomes at least 0.5% by volume and smashing the oxidation reaction mixture at a temperature of 140° to 230° C. to decrease the average particle diameter of terephthalic acid by at least 20% from its average particle diameter before smashing, and (2) a second purifying step of feeding a gas containing molecular oxygen to the slurry from the first purifying step in such a proportion that the concentration of oxygen in the off-gas becomes 0.05 to 5% by volume, and contacting the slurry with the molecular oxygen-containing gas at a temperature at least 10° C. higher than in the first purifying step and within the range of 180° to 300° C., are performed successively, and the resulting purified slurry is subjected to solid-liquid separation to recover terephthalic acid.

The essential feature of the present invention is that the aforesaid specified first and second purifying steps are performed in this sequence subsequent to a main reaction step of oxidizing p-xylene with molecular oxygen in the presence of a heavy metal compound and a bromine compound in an acetic acid solvent to an extent of at least 90 mole % based on the p-xylene fed. It has been found that the effects or advantages of this invention can be exhibited only by the combination of these two purifying steps, and the object of this invention cannot be achieved if only one of these purifying steps is carried out. Specifically, when only the first purifying step is carried out, the decrease of 4-CBA and coloring materials in the resulting terephthalic acid product is small, and when the resulting terephthalic acid is mixed with a glycol, the resulting slurry has a high viscosity. Hence, the terephthalic acid is not suitable for producing polyesters advantageously by direct polymerization. On the other hand, when only the second purifying step is performed by omitting the first one, the purifying effect cannot be easily increased, and it is necessary to perform the treatment for long periods of time at high temperatures. This is economically disadvantageous, and the amount of coloring materials in the resulting terephthalic acid is larger than that in the process of this invention.

The process of this invention will be described below in detail.

Production of terephthalic acid by oxidation of p-xylene with molecular oxygen in the main reaction step of the process of this invention can be effected by methods known per se (see, for example, U.S. Pat. No. 2,833,816). Any method can be applied which comprises reacting p-xylene with molecular oxygen in the presence of a catalyst comprising a heavy metal compound and a bromine compound in an acetic acid solvent. The heavy metal compound which can be used as a catalyst component in this process is a compound containing at least one metal selected from, for example, cobalt, manganese, cerium, nickel, iron, and chromium. Specific examples include cobalt acetate, manganese acetate, cerium acetate, cobalt naphthenate, manganese naphthenate, cobalt carbonate and manganese carbonate. The bromine compound to be used in combination with the heavy metal compound includes inorganic compounds such as the alkali metal salts, alkaline earth metal salts and heavy metal salts of bromine, and hydrogen bromide, and organic compounds such as alkyl bromides. Specific examples of suitable bromine compounds are sodium bromide, hydrogen bromide, tetrabromoethane, and bromides of the aforesaid heavy metals such as cobalt bromide and manganese bromide. When a heavy metal-containing compound is used as the bromine compound, it can simultaneously play the role of the heavy metal compound, and therefore, the heavy metal compound can be omitted.

At times, two or more heavy metal compounds are desirably used in combination, and particularly, the combined use of manganese and cobalt compounds is preferred. Advantageously, they are used in a Mn/Co weight ratio of 0.2-3/1.

The amounts of the heavy metal compound and bromine compound used are not strictly limited. Generally, 0.01 to 0.2 part by weight of the heavy metal compound as metal is used per 100 parts by weight of the solvent such as acetic acid, and the bromine/heavy metal atomic ratio is from 1 to 6.

The main reaction step comprising oxidizing p-xylene with molecular oxygen in the presence of heavy metal and bromine compounds in acetic acid to form terephthalic acid can be carried out by methods known per se. There is no particular restriction on the reaction conditions in the main reaction step. It is important however that in practicing the process of this invention, at least 90 mole % of p-xylene fed be oxidized (namely, the conversion of p-xylene be at least 90%). It is necessary therefore to select the composition and amount of the catalyst, the reaction temperature and the residence time in such a way that at least 90 mole % of p-xylene fed to the main reaction step is oxidized. The reaction temperature is generally 150° to 250° C., preferably 180° to 230° C. The residence time is usually 10 to 240 minutes. Molecular oxygen as the oxidizing agent is generally air or an oxygen gas diluted with an inert gas. The amount of molecular oxygen is 3.0 to 4.5 moles per mole of p-xylene. Those skilled in the art would be able to determine easily the reaction conditions which give a p-xylene conversion of at least 90 mole %, by properly selecting the composition of the catalyst, the reaction temperature and the residence time through a simple routine test.

Generally, the conversion increases as the concentration of the catalyst becomes higher, the reaction temperature becomes higher, or the residence time becomes longer. Preferably, therefore, the reaction conditions are determined by considering these factors. The p-xylene conversion of at least 90% can be achieved even when the reaction conditions are outside the above-described preferred temperature and time conditions. But in view of economy and the quality of the resulting terephthalic acid, it is recommended to perform oxidation of p-xylene within the aforesaid temperature and time ranges. If in the process of this invention, the conversion of p-xylene in the main reaction step is less than 90%, the load on the oxidation reaction in the first purifying step becomes too high, and the pulverizing effect is undesirably reduced. On the other hand, if the conversion of p-xylene is too high, it is economically disadvantageous. Preferably, the conversion of p-xylene is adjusted to not more than 99.9%, preferably to 98 to 99.95%.

Thus, the main oxidation reaction step gives an oxidation reaction mixture in slurry form composed of the resulting crystals of terephthalic acid and a mother liquor containing the catalyst components, the unreacted xylene, oxidation reaction intermediates of xylene, the acetic solvent, etc. The reaction mixture can be directly submitted to the first purifying step to be described.

The oxidation reaction intermediates of xylene, as referred to herein, denote compounds in various oxidation states formed during the oxidation reaction leading to terephthalic acid, and mainly include 4-carboxybenzaldehyde (to be abbreviated as "4-CBA"), p-toluic acid (to be abbreviated as "PTA"), and p-acetoxymethylbenzoic acid (to be abbreviated as "PAMBA"). PAMBA is represented by the following structural formula (I) and exists in the mother liquor of the oxidation reaction mixture of p-xylene together with p-hydroxymethylbenzoic acid (PHMBA) of the following structural formula (II).

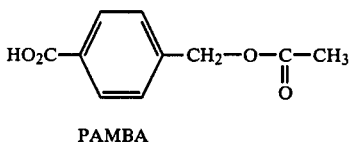

PAMBA

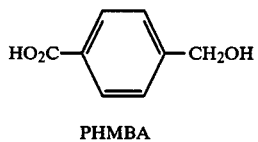

PHMBA

These are in equilibrium in the mother liquor as shown below.

$$(I) + H_2O \rightleftharpoons (II) + CH_3COOH \tag{1}$$

Accordingly, it should be understood that both the compounds (I) and (II) are referred to herein inclusively as PAMBA. The amounts of (I) and (II) in the oxidation reaction mixture vary greatly depending upon the oxidation reaction conditions. Generally, the amount of the compound (I) is nearly the same as that of 4-CBA, and the amount of the compound (II) is from ⅓ to 1/10 of the amount of the compound (I).

p-Tolualdehyde, p-methylbenzyl alcohol, p-methylbenzyl acetate, benzyl bromide derivatives, etc. also exist as the oxidation reaction intermediates. But in performing the main reaction step in this invention, the total concentration of PTA, 4-CBA and PAMBA in the oxidation reaction step is an important factor. Specifically, the effect of the present invention increases further when the total concentration of these three oxidation reaction intermediates present in the mother liquor of the slurry-like oxidation reaction mixture to be submitted to the first purifying step is adjusted generally to at least 1,500 ppm but not more than 40,000 ppm, preferably to 2,000 to 30,000 ppm. The concentration of the intermediates can be adjusted, for example, by (A) properly selecting the reaction conditions in the main reaction step, i.e. the concentration or feed rate of p-xylene, the reaction temperature, the catalyst, etc.; (B) diluting or replacing the resulting oxidation reaction mixture with a solvent or concentrating the oxidation reaction mixture; or (C) adding or removing reaction intermediates. The method (c), however, is complex in steps and is not economically feasible. Advantageously, the concentration of the reaction intermediates is adjusted to the aforesaid range by performing the methods (A) and (B) either singly or in combination.

If the total concentration of the oxidation reaction intermediates is less than 1,500 ppm, the terephthalic acid crystals are difficult to smash in the subsequent first purifying step and the purifying efficiency is low. For this reason, even if terephthalic acid obtained through the second purifying step is of high purity, the industrial advantage of the process tends to be reduced since the economy of the process is evaluated by the total sum of the amount of acetic acid burnt and the amount of energy consumed. When the total concentration exceeds 40,000 ppm, the terephthalic acid crystals are difficult to smash in the first purifying step, and burning of acetic acid which occurs simultaneously with re-oxidation increases, resulting in a tendency to reduce the economy of the process.

According to one preferred embodiment of this invention, the total concentration of PTA, 4-CBA and PAMBA in the mother liquor of the oxidation reaction mixture obtained in the main reaction step which is to be submitted to the first purifying step is controlled to the range of 1,500 to 40,000 ppm, preferably 2,000 to 30,000 ppm, in addition to oxidizing at least 90 mole % of p-xylene fed to the main reaction step. If the oxidation reaction mixture obtained in the main reaction step is to be directly subjected to the first purifying step, it is preferred to select the reaction conditions of the main reaction step such that the total concentration of the reaction intermediates in the mother liquor of the reaction mixture obtained in the main reaction step becomes 1,500 to 40,000 ppm. To obtain such conditions, it is necessary to select the composition of the catalyst, the reaction temmperature and the concentration and feed rate of p-xylene carefully. For example, when the composition and concentration of the catalyst are constant, the total concentration of the oxidation reaction intermediates increases as the reaction temperature is lowered. Furthermore, at a constant temperature, the concentration of the intermediates increases as the concentration of the catalyst is decreased. Furthermore, the concentration of water in the reaction mixture can affect the concentration of the intermediates. Specifically, when the composition of the catalyst and the reaction temperature are constant, the total concentration of the oxidation reaction intermediates tends to increase as the concentration of water increases. The reaction conditions should be set up by considering these relations and tendencies.

The first purifying step of this invention will now be described.

In this step, smashing of the terephthalic acid crystals formed and reoxidation of the oxidation reaction intermediates are mainly carried out. The oxidation reaction mixture obtained in the main reaction step consists mainly of terephthalic acid crystals and the mother liquor and is in the form of a slurry. In the first purifying step, most of the oxidation reaction intermediates contained in the mother liquor and a part of the oxidation reaction intermediates contained in the terephthalic acid crystals are oxidized to convert them to terephthalic acid and to reduce the amount of the oxidation reaction intermediates. In addition, the terephthalic acid particles are smashed to decrease their diameter. Thus, the first purifying step is a preparatory step for going to the second purifying step.

The oxidation reaction mixture obtained in the main reaction step may be subjected to the first purifying step either directly or after it has been diluted with a solvent or removing a part of the solvent from it. The solids concentration of the slurry in the first purifying step may be any at which it can be maintained flowable. To perform smashing and purification efficiently, it is preferably 20 to 70% by weight in general, and especially 22 to 65% by weight.

Smashing of the terephthalic acid crystals in the first purifying step can be performed by methods known per se, for example a method which involves vane smashing by high-speed agitation in a tank equipped with an agitator; a method involving using the smashing power of a centrifugal pump; a method utilizing a known wet-type smasher; a method utilizing impact due to a fall in temperature and pressure between the main oxidation reactor and the first purification tank; and a method which comprises elevating the pressure of the oxidation reaction mixture, then releasing the pressure, and utilizing impact due to this pressure difference. The average particle diameter of terephthalic acid in the oxidation reaction mixture obtained in the main reaction step varies depending upon the method of oxidation, but is generally at least 30 microns, and in many cases at least 100 microns. The goal of smashing is that the degree of smashing amounts to at least 20%, preferably at least 40%. The "degree of smashing" as referred to in the present application denotes a value calculated by the following equation.

$$\text{Degree of smashing (\%)} = \frac{A - B}{A} \times 100$$

where A is the average particle diameter of terephthalic acid crystals before the smashing treatment, and B is the average particle diameter of terephthalic acid crystals after the smashing treatment.

The advantages of the present invention increase as the degree of smashing is increased. But in view of the equipment or the efficiency of energy, it is not advisable to increase the degree of smashing to more than 95%. The most preferred degree of smashing is in the range of 40 to 90%. The average particle diameter of terephthalic acid as referred to in the present specification and claims denotes a weight average particle diameter which can be determined by measuring it while classifying the terephthalic acid crystals on a sieve using a water shower.

The treating temperature in the first purifying step is 140° to 230° C., preferably 160° to 210° C. If the treating temperature exceeds 230° C., the rate of re-oxidation of the oxidation reaction intermediates in the mother liquor increases, but the burning of acetic acid abruptly increases and moreover, the amount of coloring materials in the resulting terephthalic acid tends to increase. On the other hand, when the temperature is less than 140° C., the rate of re-oxidizing the oxidation reaction intermediates in the mother liquor is slow, and the terephthalic acid crystals are difficult to smash. Furthermore, a large amount of thermal energy is undesirably required to elevate the temperature for the second purifying step.

The gas containing molecular oxygen required for the oxidation in the first purifying step may, for example, be air or a mixture of oxygen and another gas (for example, the off-gas from the main reaction step). The amount of the molecular oxygen-containing gas to be introduced can be varied depending upon the amounts of the oxidation reaction intermediates in the oxidation reaction mixture obtained in the main reaction step which is to be subjected to the first purifying step, and the treating conditions in the first purifying step. It is necessary however to introduce it in such a proportion that the concentration of oxygen in the off-gas from the first purifying step becomes at least 0.5% by volume. If the oxygen concentration is less than 0.5% by volume, the amount of coloring components in the terephthalic acid treated in the first purifying step increases, and they adversely affect the purification in the second purifying step. The preferred concentration of oxygen in the off-gas is 1 to 8% by volume.

Generally, in the first purifying step, molecular oxygen is introduced into the inside of the oxidation reaction mixture subjected to the first purifying step. Preferably, care is taken so that the reaction mixture does not experience an oxygen-deficient state during transition from the main reaction step to the first purifying step. Accordingly, when an apparatus for carrying out the process of this invention continuously is used, it is preferable to use at the same time a method involving introducing a gas containing molecular oxygen into a conveying line for the oxidation reaction mixture from the main reaction step to the first purifying step so that molecular oxygen exists also in the conveying line. This serves to achieve the effect of this invention accurately.

In the first purifying step, the smashing treatment and the introduction of the molecular oxygen-containing gas can be simultaneously performed in the same apparatus. For example, these procedures may be carried out in a tank equipped with a high-speed agitator and an inlet through which the molecular oxygen-containing gas is introduced into the tank (in this case, too, the smashing and the introduction of the molecular oxygen-containing gas need not always to be carried out simultaneously, and can be carried out sequentially). Or there may be used a method in which a treating vessel equipped with a pump is used as a smasher, and while the slurry is circulated, the terephthalic acid is smashed in the pump portion, and the molecular oxygen-containing gas is introduced into the treating vessel to perform reoxidation. In practicing the latter in which the smashing and the introduction of the molecular oxygen-containing gas are carried out in different portions, it is desirable to shorten the residence time in the smasher portion or cause molecular oxygen to be present in this portion so that the oxidation reaction mixture in this portion is not exposed to an oxygen-deficient state for a long time. It is desirable to adjust by such a method the concentrations of the oxidation reaction intermediates in the mother liquor of the slurry to be subjected to the second purifying step so that the concentration of 4-CBA becomes 10 to 1000 ppm, preferably 20 to 400 ppm.

The first purifying step is carried out under the conditions described above. The effects of this invention are very great when the total concentration of PTA, 4-CBA and PAMBA, the oxidation reaction intermediates in the mother liquor of the oxidation reaction mixture in slurry form is within the above-specified range. Specifically, the reoxidation of the oxidation reaction intermediates in the first purifying step proceeds easily. Furthermore, the terephthalic acid crystals can be easily smashed, and with the smashing, the effect of removing the impurities in the terephthalic acid particles increases. This effect can also be obtained by feeding a small amount of an alkylbenzene into the first purifying step. It is not known why such an effect is produced, but it is presumed that the catalyst in the reaction mixture is activated by radical species generated from the oxidation reaction intermediates present in the oxidation reaction mixture to be submitted to the first purifying step or by radical species generated from the small amount of the freshly supplied alkylbenzene, and consequently, the oxidation reaction intermediates in the mother liquor are rapidly oxidized. With regard to the smashing, it is presumed that by the presence of moderate amounts of PTA, 4-CBA and PAMBA or by the oxidation of the small amount of the freshly added alkylbenzene, the co-existing terephthalic acid particles temporarily become coarse particles having a weak bonding force, and therefore, they can be easily smashed and the purifying efficiency incident to the smashing increases.

The alkylbenzene to be added as required to the oxidation reaction mixture in the first purifying step of this invention is, for example, a benzene derivative having at least one (preferably 1 or 2) alkyl group in the benzene skeleton. Specific examples include toluene, ethylbenzene, xylenes, propylbenzenes, tolualdehydes and toluic acid. Of these, p-xylene and p-tolualdehyde are especially preferred because they produce an especially great effect and their oxidation products are terephthalic acid.

The amount of the alkylbenzene to be fed is preferably one corresponding to 0.01 to 5 mole % of p-xylene introduced into the main reaction step. When the concentration of the oxidation reaction intermediates in the mother liquor of the oxidation reaction mixture to be transferred to the first purifying step is low, it is advantageous to supply a relatively large amount of the alkylbenzene. When the total concentration of the oxidation reaction intermediates is within the range of 1,500 to 40,000 ppm but the catalyst components in the oxidation reaction mixture to be submitted to the first purifying step are reduced in activity for some cause, the activity of the catalyst can be increased by feeding a small amount of the alkylbenzene. This effect becomes surer by feeding a fresh supply of the catalyst components together with the alkylbenzene. If the amount of the alkylbenzene fed is too large, the load on the reaction in the first purifying step becomes high, and the efficiency of smashing and purification rather tends to decrease. It is preferred therefore to adjust the amount of the alkylbenzene to 0.02 to 2 mole % based on the p-xylene introduced into the main reaction step.

The feeding of the alkylbenzene to the first purifying step may be intermittent, but is preferably continuous. It may be fed in liquid form or as a gas together with the molecular oxygen-containing gas. In liquid form, it may be fed either as such or after it is diluted with a solvent or mixed with a solution of fresh catalyst components. The catalyst components to be mixed at this time may be a catalyst of the same composition as in the main oxidation reaction, or a bromine compound may be mainly fed to supplement the bromine component which has been consumed and inactivated in the oxidation reaction.

The slurry treated in the first purifying step is then sent to the second purifying step. One effective method of increasing the efficiency of smashing at this time is to install a liquid cyclone between the first purifying step and the second purifying step, feed the slurry smashed in the first purifying step, feeding the overflow slurry of the liquid cyclone (i.e. the slurry containing small particles of terephthalic acid which have been classified in the cyclone) to the second purifying step, and recycle the under flow of the liquid cyclone (i.e. the slurry containing large particles of terephthalic acid) to the first purifying step. The utilization of the liquid cyclone is particularly effective when applied to the continuous practice of this invention. At this time, the concentration of the slurry in the first purifying step becomes higher than that of the slurry in the second purifying step. But this does no particularly give rise to a problem in the process of this invention unless the solids concentration of the slurry in the first purifying step exceeds 70%. The liquid cyclone applicable to the process of this invention may be of a known structure, and a plurality of liquid cyclones connected to each other may also be used. When the liquid cyclone is provided between the first purifying step and the second step, the average particle diameter of terephthalic acid in the first purifying step differs from that of terephthalic acid fed to the second purifying step. It should be understood that in this case, the average particle diameter (B) of terephthalic acid crystals after the smashing treatment in the present specification and claims and in the definition of "the degree of smashing" given hereinabove denotes the average particle diameter of terephthalic acid crystals which are to be fed to the second purifying step.

The second purifying step of this invention will now be described.

The slurry which has undergone smashing and re-oxidation treatments in the first purifying step is contacted with a molecular oxygen-containing gas in the second purifying step at a temperature at least 10° C. higher than the temperature in the first purifying step and within the range of 180° to 300° C., preferably 210° to 260° C. The higher the treating temperature, the lower the viscosity of a mixture of the resulting terephthalic acid with a glycol and the smaller the amounts of the oxidation reaction intermediates typified by 4-CBA. But higher temperatures tend to increase the amount of coloring materials. On the other hand, if the treating temperature is lower than 180° C., the viscosity of a mixture of the resulting terephthalic acid and a glycol is high, and the terephthalic acid tends to be unsuitable for use in direct polymerization. Hence, the treating temperatures within the above-specified range are suitable. It is further necessary that the treating temperature used in the second purifying step be at least 10° C. higher, preferably 20° to 100° C. higher, than the temperature used in the first purifying step. If this temperature difference is less than 10° C., a purifying effect is difficult to obtain in the second purifying step.

The molecular oxygen-containing gas used in the second purifying step may, for example, be air, a mixture of oxygen and nitrogen, a mixture of oxygen and another inert gas, a mixture of air and an inert gas, or the off-gas from the main oxidation reaction step. The amount of the molecular oxygen-containing gas to be fed to the second purifying step varies depending upon the amounts of the oxidation reaction intermediates in the mother liquor and the terephthalic acid crystals which are present in the slurry to be submitted to the second purifying step and the treating conditions in the second purifying step. It is necessary however to adjust the amount of the molecular oxygen-containing gas such that the concentration of oxygen in the off-gas from the second purifying step becomes 0.05 to 5% by volume, preferably 0.1 to 2% by volume. It is especially preferred to feed the molecular oxygen-containing gas in an amount 10 to 300 times, particularly 20 to 100 times, the theoretical amount of oxygen required to oxidize PTA 4-CBA and PAMBA in the mother liquor of the slurry. If the concentration of oxygen in the off-gas is below 0.05% by volume, the amount of coloring materials in the resulting terephthalic acid tends to increase. On the other hand, if the amount of oxygen fed is increased too much, the amount of acetic acid burnt becomes large enough to bring about an economic disadvantage. In order to limit the amount of oxygen in the off-gas to be a very small value as stated above, it is advantageous for a control of the operation to use the off-gas from the main reaction step after elevating its pressure, or to use diluted air.

It is usually sufficient to perform the second purifying step for 5 to 240 minutes. The second step can be carried out by using an ordinary agitated vessel, a bubble tower, etc.

As stated in detail hereinabove, it is essential in the process of this invention to perform the main reaction step, the first purifying step and the second purifying step sequentially. For example, each of these steps may be carried out batchwise, or one or two of them may be carried out batchwise. Industrially, it is preferred to perform all of the steps continuously, namely to perform each step in a separate reactor or treating vessel and to continuously or intermittently receive in each reactor or treating vessel the starting reaction mixture or the oxidation reaction mixture in an amount corresponding to the amount of the slurry delivered therefrom so that the amount of the slurry in each reactor or treating vessel is always maintained nearly constant.

Following the second purifying step, the slurry from the second purifying step is separated into terephthalic acid and the mother liquor in accordance with a method known per se. Preferably, prior to this solid-liquid separation, the slurry is passed through a receiving vessel which is kept at a lower temperature and a lower pressure than in the second purifying step. The separated terephthalic acid is worked up by a method known per se, for example by washing. Thus, there can be obtained terephthalic acid of high purity having such a quality and properties as to enable it to be used in direct polymerization with a glycol component.

In the present specification and claims, the concentration of oxygen in the off-gas denotes the concentration of oxygen in a dry gas obtained by removing condensable components such as acetic acid and water from the off-gas discharged from a given step.

The concentrations of PTA (p-toluic acid) and PAMBA (p-acetoxymethylbenzoic acid) in the mother liquor means the concentrations of these compounds in the reaction mother liquor resulting from separation of terephthalic acid crystals from the oxidation reaction mixture obtain in the main reaction step. These concentrations were measured by gas chromatography after the mother liquor has been concentrated under reduced pressure at a low temperature and converted to a methyl ester. The concentration of 4-CBA (4-carboxybenzaldehyde) is measured by polarography.

The "optical density", one parameter expressing the quality of terephthalic acid, denotes the absorbance of a solution of 4 g of terephthalic acid in 50 ml of 2N potassium hydroxide solution, which is measured at a wavelength of 340 nm using a cell having a light path length of 5 cm.

The "slurry viscosity", another parameter expressing the quality of terephthalic acid, denotes the viscosity of a dispersion of 1 mole of terephthalic acid in 1.6 moles of ethylene glycol, which is measured at 230° C. by a B-type viscometer.

The following Examples and Comparative Examples illustrate the present invention more specifically. It should be understood however that the invention is not limited to these examples.

The "main reaction mixtures" used in the following examples were produced as follows:

Sample 1

An acetic acid solution containing 4% by weight of water, 20% by weight of p-xylene, 0.08% by weight of cobalt acetate tetrahydrate, 0.1% by weight of manganese acetate tetrahydrate and 0.1% by weight of sodium bromide and air were fed at a rate of 2.8 liters/hr and 40 liters/min., respectively, into a 5-liter titanium autoclave equipped with an agitator, and reacted at a temperature of 210° C. and a pressure of 22 kg/cm$^2$ with a residence time of 60 minutes. The reaction mixture was withdrawn together with the reaction gas into a receiving vessel equipped with a condenser, and quickly cooled so as to avoid oxygen deficiency due to high temperature. The resulting sample had the following compposition.

Amount of terephthalic acid per kg of the reaction mixture: 250 g

Concentration of PTA in the mother liquor: 6100 ppm

Concentration of 4-CBA in the moher liquor: 1510 ppm

Concentration of PAMBA in the mother liquor: 1230 ppm

Total concentration of PTA, 4-CBA and PAMBA: 8840 ppm

The quality of a product obtained by washing 100 g of the cake of terephthalic acid in the reaction mixture with hot acetic acid was expressed as follows:

4-CBA content: 2100 ppm

Optical density: 0.525

Average particle diameter: 138 microns

Sample 2

The procedure in the preparation of sample 1 was repeated except that the reaction temperature was changed to 220° C.

The resulting sample had the following composition.

Amount of terephthalic acid per kg of the reaction mixture: 254 g

Concentration of PTA in the mother liquor: 800 ppm

Concentration of 4-CBA in the mother liquor: 365 ppm

Concentration of PAMBA in the mother liquor: 295 ppm

Total concentration of PTA, 4-CBA and PAMBA: 1460 ppm

The quality of a product obtained by washing 100 g of the cake of terephthalic acid in the reaction mixture with hot acetic acid had the following quality.

4-CBA content: 410 ppm

Optical density: 0.142

Average particle diameter: 115 microns

Main reaction mixtures (samples 3 to 5) having the properties shown in Table 1 were prepared by varying the reaction conditions in the above procedure.

Sample 6

An acetic acid solution containing 4% by weight of water, 20% by weight of p-xylene, 0.1% by weight of cobalt acetate tetrahydrate, 0.1% by weight of manganese acetate tetrahydrate and 0.13% by weight of tetrabromoethane and air were fed into the same apparatus as used in the preparation of sample 1 at a rate of 2.8 liters/hr and 40 liters/min., respectively, and reacted at a temperature of 212° C. and a pressure of 24 kg/cm$^2$ with a residence time of 60 minutes. The resulting sample had the quality shown in Table 1.

Sample 7

The procedure of the preparation of sample 6 was repeated except that 0.1% by weight, as HBr, of hydrobromic acid (47% aqueous solution) was used instead of tetrabromoethane. The resulting sample had the quality shown in Table 1.

TABLE 1

| Sample | Concentration in the mother liquor of the main reaction mixture (ppm) | | | | Quality of terephthalic acid in the main reaction mixture | | | Conversion of p-xylene (%) |
| --- | --- | --- | --- | --- | --- | --- | --- | --- |
| | PTA | 4-CBA | PAMBA | Total | 4-CBA content (ppm) | Optical density | Average particle diameter (microns) | |
| 1 | 6,100 | 1,510 | 1,230 | 8,840 | 2,100 | 0.525 | 138 | 98.8 |
| 2 | 800 | 365 | 295 | 1,460 | 410 | 0.142 | 114 | 99.6 |
| 3 | 4,300 | 1,050 | 980 | 6,330 | 970 | 0.373 | 126 | 99.1 |
| 4 | 16,300 | 3,500 | 2,800 | 22,600 | 3,600 | 0.710 | 149 | 97.2 |
| 5 | 35,000 | 4,600 | 3,800 | 43,400 | 5,900 | 0.950 | 182 | 96.3 |
| 6 | 7,400 | 1,820 | 1,453 | 10,670 | 2,085 | 0.688 | 141 | 98.4 |
| 7 | 6,700 | 1,740 | 1,320 | 9,760 | 1,930 | 0.655 | 139 | 98.8 |

EXAMPLE 1

A 5-liter titanium autoclave A equipped with a reflux condenser, an agitating device, a slurry feeding device, a p-alkylbenzene feeding device and a treated slurry discharge opening and a device B of the same specification as the autoclave A were connected by a slurry conveying line. The main reaction mixture (sample 1) was continuously fed into the autoclave A with an average residence time of 1 hour. While the slurry was being sent to B, the agitating vane was rotated at 1800 rpm, and the slurry was smashed at a temperature of 190° C. and a pressure of 12 kg/cm$^2$ while feeding air such that the concentration of oxygen in the off-gas became 4 to 5% by volume. The smashed slurry was introduced into the device B through the slurry conveying line. The agitating vane was rotated at 850 rpm at a temperature of 230° C. and 35 kg/cm$^2$, and the slurry was treated with a residence time of 30 minutes while feeding a gaseous mixture composed of 95% by volume of nitrogen and 5% by volume of oxygen so that the concentration of oxygen in the off-gas became 0.6 to 0.9% by volume. In this manner, the main reaction mixture was treated for 7 hours, and then cooled to room temperature with a care taken not to cause oxygen deficiency in devices A and B. The solid withdrawn from the device A had an average particle diameter of 45 microns, and the concentration of 4-CBA in the mother liquor was 26 ppm. The slurry withdrawn from the device B was subjected to solid-liquid separation, and the solid was washed with 4 times its weight of hot acetic acid. The resulting purified terephthalic acid had the following quality.

4-CBA content: 210 ppm
Optical density: 0.079
Average particle diameter: 136 microns
Viscosity of the slurry: 765 centipoises

EXAMPLE 2

The main reaction mixture (sample 1) was treated in the same apparatus and under the same conditions as in Example 1 except that the temperature in the device A was changed to 160° C. The results are shown in Table 2.

EXAMPLE 3

The main reaction mixture (sample 1) was treated in the same apparatus and under the same conditions as in Example 1 except that the temperature in the device B was changed to 250° C. and the concentration of oxygen in the off-gas in the device B was changed to 0.2 to 0.4% by volume.

Comparative Example 1

The main reaction mixture (sample 1) was treated in the device A under the same conditions as in Example 1, but not subjected to treatment in the device B. The sample was cooled and the slurry was taken out and subjected to solid-liquid separation in the same way as in Example 1. The solid was treated in the same way as in Example 1 to form purified terephthalic acid. Its quality was poor as shown in Table 2, and the slurry viscosity was high.

Comparative Example 2

The reaction mixture (sample 1) was treated in the device B under the same conditions as in Example 1 without treating it in the device A. The resulting purified terephthalic acid had the quality shown in Table 2.

Comparative Example 3

The main reaction mixture (sample 1) was treated in the same apparatus and under the same conditions as in Example 1 except that air was not introduced into the device A. The resulting purified terephthalic acid had a very poor optical density as shown in Table 2.

Comparative Example 4

The main reaction mixture (sample 1) was treated in the same apparatus and under the same conditions as in Example 1 except that the concentration of oxygen in the off-gas from the device A was adjusted to 0.1 to 0.3%. The resulting purified terephthalic acid had a poor quality with a high optical density as shown in Table 2.

Comparative Example 5

The main reaction mixture (sample 1) was treated in the same apparatus and under the same conditions as in Example 1 except that the mixed gas fed into the device B was changed to a mixture of 10% by volume of oxygen and 90% by volume of nitrogen and the concentration of oxygen in the off-gas in the device B was changed to 6 to 7%. The quality of the resulting terephthalic acid was good as shown in Table 2, but the loss of carbon was great. (The loss of carbon is explained in the footnote to Table 2. It is an index showing that the solvent and the effective components of the starting mixture decompose and dissipate in the off-gas, and the larger this value, the more economically disadvantageous is the process.)

Comparative Examples 6 to 10

The main reaction mixture (sample 1) was treated in the same apparatus and under the same conditions as in Example 1 except that the temperatures of the devices A and B and the concentration of oxygen in the off-gas were changed as shown in the following table.

The results are shown in Table 2.

| Comparative Example | Device A Temperature (°C.) | Device A O₂ concentration in the off-gas (vol. %) | Device B Temperature (°C.) | Device B O₂ concentration in the off-gas (vol. %) |
|---|---|---|---|---|
| 6 | 130 | 4–7 | 230 | 0.6–0.9 |
| 7 | 190 | 4–5 | 160 | " |
| 8 | 190 | " | 190 | " |
| 9 | 240 | 1–2 | 230 | " |
| 10 | 230 | 2–3 | 230 | " | age particle diameter of 42 microns. The resulting slurry was treated in the same apparatus and under the same conditions as in Example 1 except that the rotating speed of the agitator was changed to 400 rpm.

The quality of the resulting terephthalic acid is shown in Table 2.

Comparative Example 12

The main reaction mixture (sample 1) was smashed in the same way as in Comparative Example 11. The resulting solid had an average particle diameter of 44 microns.

The resulting slurry was treated in the same apparatus and under the same conditions as in Example 1 except that the rotating speed of the agitator in the device A was changed to 400 rpm, and 0.5 mole %, based on the cruded terephthalic acid, of p-xylene was fed.

The results are shown in Table 2.

TABLE 2

| Example (Ex.) or Comparative Example (CEx.) | Product withdrawn from device A after cooling — Average particle diameter (μ) | Product withdrawn from device A after cooling — 4-CBA concentration in the mother liquor (ppm) | Quality of purified terephthalic acid — 4-CBA content (ppm) | Quality of purified terephthalic acid — Optical density | Quality of purified terephthalic acid — Average particle diameter (μ) | Quality of purified terephthalic acid — Viscosity of the slurry (c.p.) | Degree of purification (*1) | Loss of Carbon (*2) |
|---|---|---|---|---|---|---|---|---|
| Ex. 1 | 45 | 26 | 210 | 0.079 | 136 | 765 | 90 / 85 | 100 |
| Ex. 2 | 32 | 173 | 295 | 0.089 | 144 | 710 | 86 / 83 | 103 |
| Ex. 3 | 44 | 28 | 170 | 0.089 | 152 | 690 | 92 / 83 | 108 |
| CEx. 1 | 45 | 28 | 960 | 0.412 | 45 | 6240 | 54 / 22 | 90 |
| CEx. 2 | — | — | 651 | 0.242 | 140 | 725 | 69 / 54 | 105 |
| CEx. 3 | 41 | 2050 | 1030 | 1.92 | 160 | 685 | 51 / −266 | 125 |
| CEx. 4 | 55 | 1210 | 860 | 1.625 | 161 | 660 | 59 / −210 | 107 |
| CEx. 5 | 46 | 24 | 185 | 0.068 | 136 | 760 | 91 / 87 | 182 |
| CEx. 6 | 30 | 1500 | 430 | 0.765 | 148 | 700 | 80 / −46 | 125 |
| CEx. 7 | 46 | 25 | 1120 | 0.232 | 44 | 6320 | 47 / 56 | 96 |
| CEx. 8 | 45 | 27 | 798 | 0.221 | 76 | 1970 | 62 / 58 | 99 |
| CEx. 9 | 60 | 8 | 240 | 0.863 | 122 | 830 | 89 / −64 | 153 |
| CEx. 10 | 56 | 13 | 245 | 0.423 | 128 | 780 | 88 / 19 | 148 |
| CEx. 11 | 108 | 22 | 453 | 1.583 | 123 | 842 | 78 / −202 | 98 |
| CEx. 12 | 114 | 18 | 370 | 1.463 | 121 | 845 | 82 / −179 | 98 |

Note to Table 2
(*1) The degree of purification is an index showing how much improvement in quality was achieved in the devices A and B over the terephthalic acid cake in the main oxidation reaction mixture and is represented by the following.

$$100 \times \left(1 - \frac{\text{4-CBA concentration (or optical density) of purified terephthalic acid}}{\text{4-CBA concentration (or optical density) of the solid in the sample used}}\right)$$

(*2) The loss of carbon is the relative value of the quotient of the amount of carbon components (carbon dioxide gas, carbon monoxide, methane and methyl acetate) in the off-gases from the devices A and B during the main reaction and purification divided by the amount of terephthalic acid formed, which is calculated by taking this quotient in Example 1 as 100.

Comparative Example 11

The main reaction mixture (sample 1) was continuously fed into the same device A as used in Example 1 with an average residence time of 1 hour, and smashed at 190° C., without feeding air, while rotating the agitating vane at 1800 rpm. The resulting solid had an aver-

Comparative Example 13 and Examples 4 to 6

The main reaction mixture (sample 4) was treated in the same apparatus and under the same conditions as in Example 1 except that the rotating speed of the agitating vane in the device A was changed to 400, 1600, 1800, and 2400 rpm. The results are shown in Table 3.

TABLE 3

| Example (Ex.) or Comparative Example (CEx.) | Sample No. | Rotating speed of device A (ppm) | Product withdrawn from device A after cooling | | Quality of terephthalic acid after purification | | | | |
|---|---|---|---|---|---|---|---|---|---|
| | | | Average particle diameter (μ) | 4-CBA concentration of the mother liquid (ppm) | 4-CBA content (ppm) | Optical density | Average particle diameter (μ) | Slurry viscosity (c.p.) | Degree of purification | Loss of carbon |
| CEx. 13 | 4 | 400 | 136 | 32 | 936 | 0.320 | 124 | 830 | 74 55 | 82 |
| Ex. 4 | 4 | 1600 | 82 | 36 | 720 | 0.234 | 130 | 770 | 80 67 | 83 |
| Ex. 5 | 4 | 1800 | 55 | 41 | 540 | 0.142 | 137 | 735 | 85 80 | 82 |
| Ex. 6 | 4 | 2400 | 20 | 52 | 210 | 0.057 | 152 | 680 | 94 92 | 80 |

EXAMPLE 7 TO 12

Each of the main reaction mixtures shown in Table 4 was treated in the same way as in Example 1. The results are shown in Table 4.

TABLE 5

| Example | Sample No. | Amount of p-xylene charged into device A (%) (*) | Product withdrawn from device A after cooling | | Quality of terephthalic acid after purification | | | | | |
|---|---|---|---|---|---|---|---|---|---|---|
| | | | Average particle diameter (μ) | 4-CBA concentration in the mother liquor (ppm) | 4-CBA content (ppm) | Optical density | Average particle diameter (μ) | Slurry viscosity (c.p.) | Degree of purification | Loss of carbon |
| 13 | 1 | 0.5 | 38 | 18 | 147 | 0.058 | 142 | 720 | 93 89 | 101 |
| 14 | 1 | 1.5 | 35 | 20 | 168 | 0.063 | 150 | 690 | 92 88 | 103 |
| 15 | 1 | 1.5 | 35 | 12 | 105 | 0.053 | 151 | 690 | 94 90 | 103 |

(*) The percentage is mole % based on crude terephthalic acid fed to device A.

TABLE 4

| Example | Sample No. | Product withdrawn from device A after cooling | | Quality of terephthalic acid after purification | | | | | |
|---|---|---|---|---|---|---|---|---|---|
| | | Average particle diameter (μ) | 4-CBA concentration in the mother liquor (ppm) | 4-CBA content (ppm) | Optical density | Average particle diameter (μ) | Slurry viscosity (c.p.) | Degree of purification | Loss of carbon |
| 7 | 2 | 67 | 18 | 62 | 0.043 | 120 | 905 | 83 70 | 162 |
| 8 | 3 | 52 | 23 | 126 | 0.052 | 132 | 758 | 87 86 | 131 |
| 9 | 4 | 41 | 48 | 360 | 0.121 | 141 | 720 | 90 83 | 82 |
| 10 | 5 | 72 | 650 | 472 | 0.423 | 150 | 690 | 92 55 | 132 |
| 11 | 6 | 44 | 24 | 229 | 0.117 | 140 | 725 | 89 83 | 102 |
| 12 | 7 | 41 | 22 | 251 | 0.106 | 138 | 745 | 87 84 | 104 |

EXAMPLES 13 AND 14

The main reaction mixture (sample 1) was treated in the same apparatus and under the same conditions as in Example 1 except that p-xylene was charged into the device A in an amount of 0.5 mole % and 1.5 mole %, respectively. The results are shown in Table 5.

EXAMPLE 15

The main reaction mixture (sample 1) was treated in the same apparatus and under the same conditions as in Example 1 except that 1.5 mole %, based on crude terephthalic acid, of p-xylene was charged into the device A in the form of an acetic acid solution of p-xylene and the catalyst having the same composition as in the preparation of sample 1. The results are shown in Table 5.

EXAMPLE 16

In the apparatus of Example 1, a small-sized liquid cyclone was installed between the autoclaves A and B. The slurry from the autoclave A was fed into the liquid cyclone. While feeding the overflow of the liquid cyclone was sent to B and the underflow to A, the reaction mixture was continuously treated under the same conditions as in Example 1. The solid in the slurry withdrawn from A during the continuous treatment had an average particle diameter of 85 microns, and the concentration of 4-CBA in the mother liquor was 40 ppm.

The amount of terephthalic acid per kg of the reaction mixture was 350 g. The solid of the slurry withdrawn as the overflow of the liquid cyclone during the treatment had an average particle diameter of 20 microns, and the amount of terephthalic acid per kg of the mixture was 255 g. The concentration of 4-CBA in the mother liquor was 40 ppm. After the treatment, the treated reaction mixture was withdrawn and worked up in the same way as in Example 1. The purified terephthalic acid in the autoclave B thus obtained had the following quality.

4-CBA content: 170 ppm
Optical density: 0.078
Average particle diameter: 140 microns
Slurry viscosity: 750 centipoises
Degree of purification: 4-CBA 92%, optical density 86%
Loss of carbon: 100

What is claimed is:

1. In a process for producing terephthalic acid suitable for use in direct polymerization, which comprises oxidizing p-xylene with molecular oxygen in an acetic acid solvent in the presence of a heavy metal compound and a bromine compound, the improvement wherein after a main reaction step of oxidizing at least 90 mole % of p-xylene fed has been performed,
(1) a first purifying step of feeding a gas containing molecular oxygen to the oxidation reaction mixture in slurry form obtained from the main reaction step and containing p-toluic acid, 4-carboxybenzaldehyde and p-acetoxymethylbenzoic acid in a total concentration of from 2,000 ppm to 40,000 ppm in the mother liquor, said gas being in such a proportion that the concentration of oxygen in the off-gas becomes at least 0.5% by volume while smashing the oxidation reaction mixture at a temperature of 140° to 230° C. to decrease the average particle diameter of terephthalic acid by at least 20% from its average particle diameter before smashing, and
(2) a second purifying step of feeding a gas containing molecular oxygen to the slurry from the first purifying step containing 4-carboxybenzaldehyde in a concentration of from 10 to 1,000 ppm in the mother liquor, said gas being in such a proportion that the concentration of oxygen in the off-gas becomes 0.05 to 5% by volume, and contacting the slurry with the molecular oxygen-containing gas at a temperature at least 10° C. higher than in the first purifying step and within the range of 180° to 300° C.,
are performed successively, and the resulting purified slurry is subjected to solid-liquid separation to recover terephthalic acid.

2. The process according to claim 1 wherein 0.01 to 5 mole %, based on the p-xylene introduced into the main reaction step, of an alkylbenzene is added to the oxidation reaction mixture in the first purifying step.

3. The process according to claim 2 wherein the alkylbenzene is selected from p-xylene and p-tolualdehyde.

4. The process according to claim 1 wherein the reaction temperature in the main reaction step is 150° to 250° C.

5. The process according to claim 1 wherein the treating temperature in the first purifying step is 160° to 210° C.

6. The process according to claim 1 wherein the concentration of oxygen in the off-gas in the first purifying step is 1 to 8% by volume.

7. The process according to claim 1 wherein in the first purifying step, the average particle diameter of terephthalic acid is reduced to at least 40% of that before the smashing treatment.

8. The process according to claim 1 wherein the treating temperature in the second purifying step is 210° to 260° C.

9. The process according to claim 1 wherein the concentration of oxygen in the off-gas in the purifying step is 0.1 to 2% by volume.

10. The process according to claim 1 wherein the main reaction step, the first purifying step and the second purifying step are sequentially performed in a continuous manner.

11. The process according to claim 1 wherein the slurry to be subjected to the second purifying step is an overflow slurry from a liquid cyclone installed between the first purifying step and the second purifying step.

* * * * *